United States Patent [19]
Hamilton et al.

[11] Patent Number: 6,159,201
[45] Date of Patent: *Dec. 12, 2000

[54] DEVICE FOR REGIONAL IMMOBILIZATION OF A COMPLIANT BODY

[75] Inventors: George Andrew York Hamilton, Winnipeg, Canada; William G. Lindsay, Edina, Minn.

[73] Assignee: Millennium Cardiac Strategies, Inc., Edina, Minn.

[*] Notice: This patent is subject to a terminal disclaimer.

[21] Appl. No.: 09/250,719

[22] Filed: Feb. 16, 1999

Related U.S. Application Data

[63] Continuation of application No. 08/818,795, Mar. 14, 1997, Pat. No. 5,885,271.

[51] Int. Cl.$^7$ .................................................. A61B 17/00
[52] U.S. Cl. ................................................ 606/1; 600/201
[58] Field of Search ........................ 606/1, 166; 600/201; 604/314, 315

[56] References Cited

U.S. PATENT DOCUMENTS

| | | |
|---|---|---|
| 3,595,218 | 7/1971 | Kirkpatrick et al. . |
| 3,782,387 | 1/1974 | Falabella . |
| 3,983,863 | 10/1976 | Janke et al. . |
| 4,416,281 | 11/1983 | Cooper et al. . |
| 4,637,377 | 1/1987 | Loop . |
| 4,957,477 | 9/1990 | Lundback . |
| 4,973,300 | 11/1990 | Wright . |
| 5,009,660 | 4/1991 | Clapham . |
| 5,117,822 | 6/1992 | Laghi . |
| 5,150,706 | 9/1992 | Cox et al. . |
| 5,222,960 | 6/1993 | Poley . |
| 5,256,132 | 10/1993 | Snyders . |
| 5,318,262 | 6/1994 | Adams . |
| 5,345,935 | 9/1994 | Hirsch et al. . |
| 5,484,391 | 1/1996 | Buckman, Jr. et al. . |
| 5,507,779 | 4/1996 | Altman . |
| 5,509,890 | 4/1996 | Kazama . |
| 5,582,580 | 12/1996 | Buckman, Jr. et al. . |

FOREIGN PATENT DOCUMENTS

WO 97/10753  3/1997  WIPO .

OTHER PUBLICATIONS

Stephen Westaby et al., Less Invasive Surgery: Consensus From the Oxford Meeting, *Ann Thorac Surg* 62:924–31 (1996).

"Medtronic Secures Heart Immobilization and Cannula Technologies for Minimally Invasive Cardiac Surgery," Medtronic Home Page @ http://www.medtronic.com/public/medtronic/news/octo.html, Jan. 10, 1997.

Gordon Slovut, "New heart–grabber aids bypass surgery," Minneapolis Star Tribune, p. B3, Apr. 3, 1997.

Declaration of George Andrew York Hamilton re: Nov. 30, 1996 Minimally Invasive Cardiac Surgery Convention.

Pilling Surgical Instruments Catalog, pp. 114–120, Pilling Co. (1993).

Lawton Catalog, p. H and p. J.

Aesculap Catalog, pp. 632–633.

Codman Surgical Product Catalog, pp. C–53–C62.

*Primary Examiner*—Michael Buiz
*Assistant Examiner*—William Lewis
*Attorney, Agent, or Firm*—Merchant & Gould P.C.

[57] ABSTRACT

The present invention is directed to a device and methods for immobilizing a localized region of a compliant body. A device of the invention includes at least two arms, an elbow region between the arms, and a suction arrangement. During use the region of the compliant material to be immobilized is flanked by the arms and a negative pressure is applied through the suction arrangement to immobilize the flanked region. The device of the invention is suited for use in medical applications, for example, coronary bypass graft surgery.

10 Claims, 5 Drawing Sheets

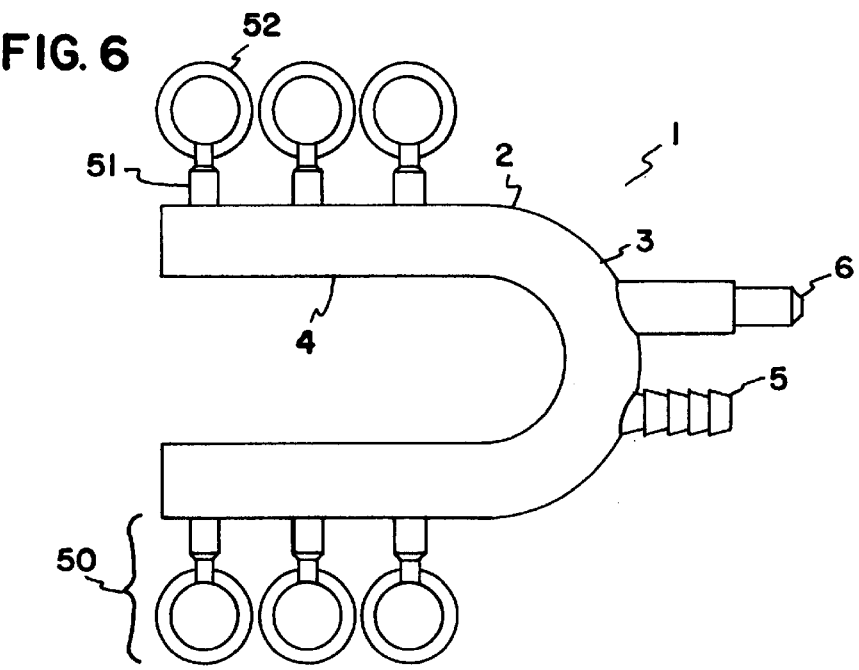
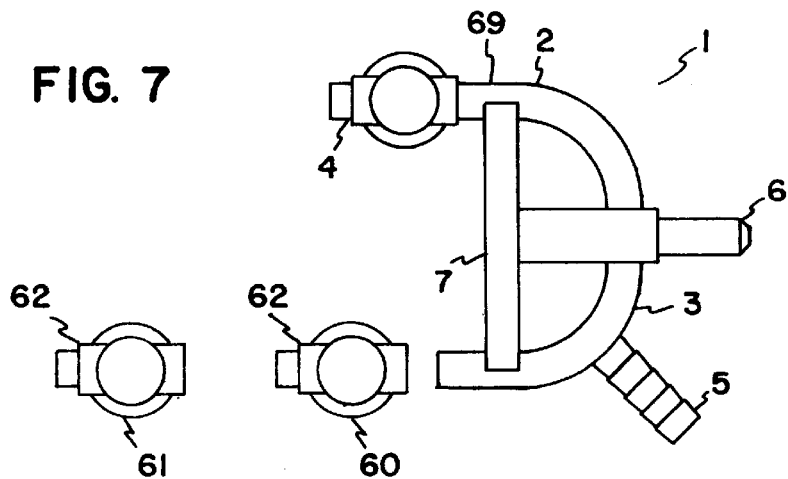
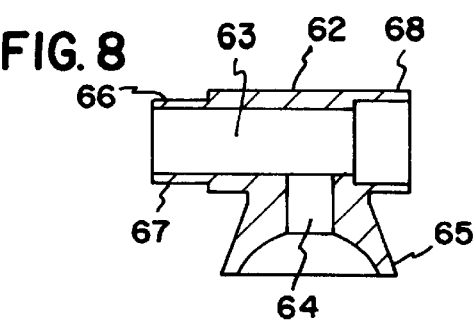

DEVICE FOR REGIONAL IMMOBILIZATION OF A COMPLIANT BODY

CROSS-REFERENCE TO RELATED APPLICATIONS

The present application is a continuation application of U.S. Ser. No. 08/818,795, filed Mar. 14, 1997 (now U.S. Pat. No. 5,885,271, issued Mar. 23, 1999) which application is incorporated herein by reference.

FIELD OF THE INVENTION

The present invention is directed to devices and methods for immobilization of a localized region of a compliant body. The invention is suited for immobilization of a localized region of a living organ without significantly compromising normal physiological function. The devices and methods are particularly suited for use in cardiovascular surgical procedures.

BACKGROUND

In general, performing an exacting procedure on a compliant material can be difficult due to the inherent evasive nature of the material. The difficulty can be exacerbated if the compliant material is mobile. One example of an exacting procedure performed on a mobile compliant material is cardiovascular surgery performed on a beating heart. Devices and methods are available for immobilizing the heart during cardiovascular surgery. However, many available systems can have undesirable effects on the patient.

Coronary artery bypass (CABG) surgery is a technique for revascularization of the heart necessitated by coronary artery obstruction. Typically, this procedure is facilitated by reducing or stopping the motion of the heart to allow for accurate suturing of the anastamoses. Present methods for reducing or stopping the motion of the heart include pharmacological and presently available mechanical means. If the heart is stopped, cardiopulmonary bypass (CPB) equipment (heart/lung machines) is used to maintain systemic blood flow. The use of pharmacological agents, with or without CPB equipment, and presently available mechanical methods to restrain the heart have inherent disadvantages.

Pharmacological agents can be used to slow or stop the heart. Usually, these drugs are administered systemically and in the case of cardioplegic agents must have a short duration of action. One disadvantage of pharmacological slowing of the heart is that the heart continues to beat thus allowing only intermittent suturing of anastomoses between beats. In addition, cardiac slowing compromises systemic circulation to vital organs thus limiting broad application of these techniques without cardiac support.

Generally, the use of cardioplegic agents necessitates use of cardiopulmonary bypass (CPB) equipment or heart/lung machines. While complete cardiac arrest allows accurate construction of anastomoses, CPB equipment is expensive to operate and can cause significant pathophysiological effects in the patient. Examples of pathophysiological consequences which can occur with CPB equipment include cardiac consequences, neurological consequences, pulmonary dysfunction, renal dysfunction, hepatic dysfunction, coagulapathies, blood element trauma and impairment of cell-mediated immunity.

Mechanical means to stabilize the heart during cardiac surgery use compression or traction to sufficiently restrain the heart to permit anastomoses of the vessels. Known mechanical devices are disclosed in, for example, U.S. Pat. Nos. 3,983,863, 4,973,300 and 5,509,890. These devices generally stabilize a localized area of the heart by compression. However, compressive forces sufficient to stabilize the heart can functionally deform the pumping chambers of the heart and impair cardiac filling or effective pumping between cardiac contractions. Hence, cardiac output is compromised. In addition, the frictional forces exerted by some devices during restraint can cause tearing or abrasion of the epicardial surface of the heart. Moreover, these devices have a limited range of access thus limiting utility of such devices to situations where only one or at most two adjacent arteries are to be bypassed.

Accordingly, there is a need for devices and methods to stabilize a compliant body during performance of an exacting procedure. In the case of living organs, there is a need to stabilize the organ without significantly compromising normal physiological function and without inducing trauma to the organ or the patient. Moreover, there is a need for devices and methods to perform exacting procedures on living organs without the use of costly patient support systems.

SUMMARY OF THE INVENTION

The present invention is directed to devices and methods to stabilize a compliant body during performance of an exacting procedure. If the compliant body is a living organ, the invention provides for stabilization of the organ without significantly compromising normal physiological function. The devices and methods disclosed herein advantageously provide for the performance of some cardiovascular surgical procedures with a reduced need for patient support systems.

The invention includes a unibody device for immobilizing a localized region of a compliant body. As fully disclosed herein, a compliant body includes an anatomical organ, such as a heart. According to the invention, the unibody device includes, at least, a frame and at least two suction arrangements coupled to the frame. The frame includes an elbow region having an angle and a first and second arm which meet at, and extend from the elbow region. At least one suction arrangement mounts to each arm of the frame. The suction arrangement includes a pod for coupling the suction arrangement to the frame, a releasable retainer mounted to the pod for engaging the compliant material and an aspiration channel that passes through the releasable retainer. The aspiration channel can communicate with known aspiration sources.

In one embodiment, the frame includes an aspiration circuit that communicates with the aspiration channel of the releasable retainer. An aspiration circuit can be internal or external to the frame. The aspiration circuit can be a "parallel" circuit by providing a vacuum directly to each releasable retainer individually. Alternatively, the aspiration circuit can be a "series" circuit by providing a vacuum to more than one releasable retainer sequentially through an aspiration circuit.

The pod component of the suction arrangement can be removably coupled to the frame. Alternatively, the pod can be integrated with the frame. The releasable retainer can be removably coupled to the pod, or the releasable retainer and pod can be integrated into a single piece.

The surface area of the region of a compliant body which can be immobilized by the unibody device is adjustable. In one embodiment, the surface area can be adjusted by extending the length of the arms. The arms of the unibody device can be extended through use of a frame insert, a frame telescope or addition of one or more extender pods. Alternatively, the surface area to be immobilized can be altered by adjusting the size of the angle between the arms. The angle can be adjusted, for example, by use of a hinge or use of a malleable material at the elbow region. The use of a malleable material at the elbow region allows for quick adjustment of the elbow angle during surgery. In another embodiment, the entire device can be prepared from a malleable material. This not only provides for adjustment of the angle at the elbow region, but it also allows for "fine tuning" the shape of the arms to follow the contours of the compliant body being stabilized.

The unibody device can include a direct vacuum inlet or an indirect vacuum inlet. A direct vacuum inlet provides a vacuum force from the source directly to the aspirator channel of the releasable retainer. In contrast, an indirect vacuum inlet provides a vacuum force from the source through an aspiration circuit that communicates with the aspiration channel of the releasable retainer.

The unibody device can also include a fixing arrangement. In one embodiment, the fixing arrangement includes a handle for manual fixation of the position of the unibody device. Alternatively, the fixing arrangement can mount the unibody to a standard surgical retractor using a fixing member that is malleable or has multiple articulations. The fixing member can mount to the retractor using, for example, a retractor clamp and one or more compression clamps.

In one embodiment, a unibody device of the invention is advantageous for stabilizing a localized region of an anatomical organ, for example, a heart during a surgical procedure. Cardiac surgical procedures which can be performed using the unibody device include coronary artery bypass graft (CABG) surgery, and tricuspid or mitral valve replacement or repair.

The devices and methods disclosed herein advantageously can be used to perform cardiovascular surgery without incurring the financial or pathophysiological costs of some patient support systems.

BRIEF DESCRIPTION OF THE DRAWINGS

FIG. 6 is a top plan view of a third embodiment of a unibody device according to the invention.

FIG. 7 is a top plan view of a fourth embodiment of a unibody device according to the invention. This embodiment includes pod extenders to extend arm length.

FIG. 8 is a cross-sectional view of an arm extender and suction arrangement used with the unibody device shown in FIG. 7.

DETAILED DESCRIPTION

Figure 1:
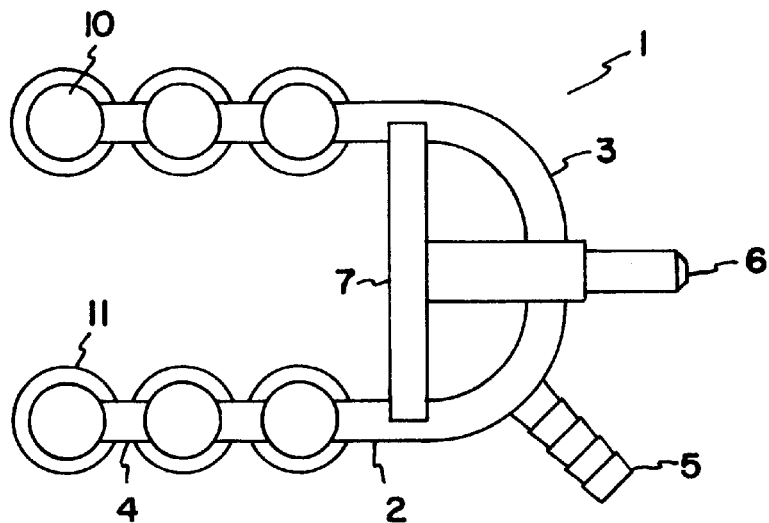
FIG. 1 is a top plan view of a first embodiment of a unibody device according to the invention.

It will be noted that in several places throughout the specification, guidance is provided through lists of examples. In each instance, the recited list serves only as a representative group. It is not meant, however, that the list is exclusive.

The invention is directed to a unibody device and method for immobilizing a localized region of a compliant material while the remainder of the material remains relatively mobile. In one embodiment, a unibody device can be used to immobilize a region of a beating heart surrounding a coronary artery during coronary artery bypass graft surgery.

As used herein, the term "unibody device" refers to a device having a single piece that is configured to flank (i.e., to place something on each side of) a region of a compliant material substantially within the perimeter of the shape of the single piece. As discussed below, in some embodiments, the single piece can include a hinging arrangement or telescoping arrangement to expand or contract the size of the region which can be flanked. The unibody device also includes two or more arms which are positioned relative to one another to provide immobilization of a region of compliant material located between at least two of the arms. Generally, the device is composed of a rigid material shaped to surround the region to be immobilized. The device can completely surround the region, however, typically it may not be necessary to completely surround the region to provide adequate immobilization.

During use, the unibody device is positioned to flank the region of the compliant material to be immobilized. Once positioned, a negative pressure is exerted from the device to draw the compliant material snugly to the device. It is believed that the combination of the negative pressure drawing the compliant material to the device and the rigid perimeter support of the device provides for the region within the perimeter of the device to be immobilized while the region external to the perimeter of the device remains relatively mobile.

In one embodiment, the unibody device is configured in a U-shape. According to this embodiment, the area to be immobilized is positioned substantially within the perimeter of the "U" and a negative pressure is applied to engage the compliant material to the U. It is not necessary that the entire perimeter surface of the device be able to exert a negative pressure on the compliant material. Generally, the negative pressure is applied at two or more locations along the arms of the U through, for example, suction cups which provide contact between the compliant material and the device. The amount of negative pressure applied need only be that which is sufficient to adequately immobilize the region of the material for the purpose immobilization is desired.

As used herein, the term "compliant material" or "compliant body" refers to any material which tends to yield elastically or flexibly when a force is applied to the material. According to the disclosure, a compliant material includes non-living materials and living materials such as skin, fascia, muscle, tendon, fat, etc. The term "compliant body" refers to a compliant material having three dimensions and includes, for example, non-living bodies and living bodies such as anatomical organs including, heart, lung, kidney, liver, intestine, bladder, etc.

When referring to a unibody device of the invention, the term "rigid" is a relative term. That is, in this context, a "rigid material" is a material which is sufficiently "non-compliant" to provide adequate immobilization of the particular compliant material on which the device is used. Hence, a rigid material can also include, for example, a hardened rubber or a malleable metal material that is flexible but has less flexibility than the compliant material on which the device may be used. The term "immobilization" is also a relative term. Generally, "immobilization" refers to sufficiently restraining the mobility of a compliant material or compliant body to permit an operator to adequately perform the procedure for which immobilization is desired.

I. Unibody Device

A unibody device according to the disclosure includes, at least, a frame and a suction arrangement. The device can also include one or more of an arm extender, an aspiration circuit, a vacuum inlet, or a fixing arrangement.

A. Frame

The "frame" of the unibody device includes an "elbow region" and at least a first and second "arm" extending from the elbow region. The "elbow region" is a region including an apex where the arms of the frame meet. The term "arm" includes the non-apical portions of the elbow region referred to as "branches," and any components mounted to the branches to extend the length dimension of the device. That is, in some embodiments, the arms include only the branches of the elbow region. In other embodiments, the arms include herein described "arm extenders" which attach to the branches or to other arm extenders to increase the length of the arm at its distal end. The "apical end" of the arm is that end nearest the apex. The "distal end" of the arm is that end farthest from the apex. The arms can be linear or non-linear. As used herein, "non-linear" includes curved, S-shaped, undulating, or other configuration which can provide flexibility in the shape or size of the surface area immobilized by the device.

The elbow region can be an apical "arch", an apical "angle" or other apical configuration. As used herein, an "arch" connotes a rounded elbow region giving the device a "U-shaped" appearance when viewed from the top of the device. An "angle" connotes a more acute intersection of the branches giving the device a "V-shaped" appearance. The terms "arch" and "angle" are used to aid in the visual description of the device, they are not to be construed as limiting the shape of the apex of the elbow region.

Generally the angle of intersection of the arms of the frame at the elbow region is about 0 degrees to about 160 degrees. In many embodiments the angle of intersection will not exceed 90 degrees, and in some embodiments will not exceed 60 degrees. When the frame is "U" shaped, the arms are essentially parallel and the "angle" of intersection is a rounded arch.

The frame of the unibody device can be made from any material suitable for the particular application of the device. For medical uses, the frame can be prepared from solid or tubular materials including metals, metal-alloys (nickel-titanium, stainless steel, etc.) and non-metals such as plastic, plexiglass, ceramic, etc. The frame can be a malleable material which advantageously provides for varying the shape of the arms of the frame to more closely follow the contours of the compliant body.

The dimensions of the frame of a unibody device can vary. Generally, the dimensions are limited only by the procedure in which the device will be used. Typically, the size of the device used for a particular application is determined by the surface area to be immobilized and by the space available in the environment where the device is used. For medical applications, the length of the unibody device from the apex to the distal end of the arms can be about 4 cm to 15 cm, and the distance between the arms, can be about 1 cm to 7 cm.

If the frame is a hollow tubular structure, the outside diameter of the tubing can be about 2 mm to 11 mm. The inside diameter can be about 0.5 mm to 9.5 mm. Preferably, the wall thickness of the tubing is at least 1.5 mm. In one presently preferred embodiment, the frame tubing has about a 4 mm inside diameter and about a 6 mm outside diameter. If the frame is a solid structure, the cross-sectional dimension of a rectangular frame structure can be about 2 mm to 12 mm by about 2 mm to 12 mm.

The surface area of a region of a compliant material which can be immobilized can be fixed for a particular unibody device. Alternatively, the surface area which can be immobilized can be adjustable. According to the invention, there are at least three ways the size of the surface area to be immobilized can be adjusted: (1) altering the size of the apex angle; (2) altering the length of the arms; or (3) altering the shape of the arms.

The size of the apex angle of a unibody device can be made adjustable by including a hinging arrangement. A hinging arrangement includes a hinge between the arms of the device at the elbow region. A hinging arrangement can also include a locking device to maintain the arms in a fixed position once the desired angle is selected. In an alternative embodiment, the angle of intersection of the arms can be adjusted by use of a malleable material which will not tend to crack or break upon repeated adjustment in the elbow region. According to this embodiment, the angle of the apex can be adjusted by pressing the arms together or pulling the arms apart to the desired size. As previously stated, the entire frame can also be prepared from a malleable material. Suitable malleable materials are known.

In yet another embodiment, the surface area between the arms can be adjusted by telescoping one branch of the frame into a second branch in the elbow region, at or near the apex. This embodiment is particularly suited for a U-shaped frame. Additional arrangements for adjusting the surface area immobilized by a unibody device are discussed below.

B. Suction Arrangement

In addition to a frame, a unibody device also includes a suction arrangement. The suction arrangement includes a region of the device which directly contacts the compliant material for engaging the compliant material to the device. The suction arrangement can also include components for increasing the surface area of the region immobilized by extending the length of the arms.

The suction arrangement includes a "pod," and a "releasable retainer." The releasable retainer includes a surface that directly contacts the compliant material and an aspiration channel through which negative pressure can flow to the contact surface of the releasable retainer. The "aspiration channel" of the releasable retainer can connect directly to an aspiration source or it can communicate with an aspiration source indirectly through a hereinbelow described "aspiration circuit." As used herein, the terms "negative pressure" and "aspiration" are synonymous and refer to a vacuum force.

In general, the pod couples the suction arrangement to the unibody device, typically on the arm of the frame. The pod also couples the releasable retainer to the unibody device. The pod can be an integrated part of the frame or it can be removably coupled to the arm. Alternatively, the pod can be an integrated part of the releasable retainer, or the releasable retainer can be removably mounted to the pod. As used here, the term "integrated" means that the components are joined as a single piece. In an embodiment of a pod that is not an integrated part of the arm, the pod can be mounted to the arm using, for example, threads, latches, clamps, clasps, rings, friction fit etc. If the pod is integrated with the frame, the pod can be mounted to the frame by welding, brazing, soldering, poured molding, etc.

The pod can be prepared from the same material as the frame. The pod can also be prepared from the same material as the releasable retainer. Alternatively, the pod can be prepared from a material different than the frame or the releasable retainer. The size and shape of the pod can vary. In some embodiments the pod can be configured and arranged to extend the length of the arm when mounted to the frame. When used as an arm extender, the pod may or may not include a continuation of the aspiration circuit to communicate a negative pressure from an aspiration source to the aspiration channel of the releasable retainer. The configuration and arrangement of the pod can provide for the releasable retainer to be mounted inside the perimeter of the frame, outside the perimeter of the frame or directly in line with the frame. In addition, the pods can be permanently fixed in relation to the frame or rotatably adjustable around the long axis of the arm to conform the angle of the plane of the contact surface with the contours of the surface of a compliant body.

The releasable retainer component of the suction arrangement includes a "contact surface", the region of the device that directly contacts the compliant material, or any covering or coating directly attached to the compliant material, that is to be immobilized. Preferably, the composition of the releasable retainer is selected from a material which is minimally irritating to the compliant material. This is particularly desirable when the compliant material is a living tissue. In one embodiment, a releasable retainer can be a suction cup. Suitable minimally irritating or nonirritating materials for a suction cup used with living tissues include, for example, rubber, silicon rubber, latex, plastic, metal alloy, etc. Known suction cups suitable for the invention are available.

The releasable retainer also includes an aspiration channel through which a vacuum from an aspiration source can flow to the contact surface of the releasable retainer. While it is conceivable that the unibody device could perform its intended function without a vacuum, for most effective functioning an aspiration channel for vacuum flow is preferred.

The releasable retainer can be removably mounted to the pod using known methods, such as threads, latches, clasps, clamps, friction fit, rings, etc. Alternatively, the releasable retainer and pod can be integrated.

The releasable retainer can be reusable. However, for hygienic purposes, when used in a medical procedure, it is foreseen that the releasable retainer will be disposed of after a single use. If the releasable retainer and pod are integrated, the pod can also be disposable. Generally, if the pod and releasable retainer are integrated, the integrated components can be prepared from a material suitable for directly contacting the compliant material, as discussed above for the releasable retainer. A reusable releasable retainer for use in a medical procedure is preferably prepared from a composition that can withstand repeated sterilization.

During use, at least one releasable retainer should be present on each arm of the unibody device. Typically, two or more releasable retainers are present on each arm. However, the number of releasable retainers on each arm does not have to be equal. The number of releasable retainers used for a particular application can vary based on the particular compliant material, the surface area to be immobilized, the procedure to be performed, etc. More than one releasable retainer can be mounted to a single pod.

C. Aspiration System

As used herein, the "aspiration system" refers to components of the unibody device which carry a negative pressure to the contact region of the releasable retainer. The "aspiration source" is any system that provides a negative pressure to the unibody device. Generally, an aspiration source for operating the unibody device is available in most surgical suites. Usually, the vacuum pressure is adjustable at the aspiration source. In one embodiment, a "vacuum control arrangement" for adjusting the vacuum pressure supplied to the device can be installed between the aspiration source and the unibody device at a location convenient for the operator to reach, for example, a foot or hand operated control. Placement of a vacuum control arrangement within the surgeon's reach is particularly desirable during cardiovascular surgery when cardiac arrest or sudden profound hypotension can necessitate quick release of the device from the heart to permit return of the heart to its normal anatomical position.

Generally a source vacuum pressure of greater than 0 mm Hg up to 400 mm Hg is suitable for operating a device of the invention. The vacuum force applied from the device for any particular procedure can vary depending on the conditions and the compliant material used. Generally, it is within the skill of the operator to determine the appropriate vacuum force to use. In a surgical procedure, suitable vacuum pressure can vary based on the tissue type, tissue condition, size of organ, desired tissue position or other factors.

A negative pressure from the aspiration source can be delivered directly to the aspiration channel of the releasable retainer by connecting the aspiration source to a "direct vacuum inlet." A "direct vacuum inlet" is a coupler for attaching the aspiration source directly to the aspiration channel of the releasable retainer. Alternatively, a negative pressure from the aspiration source can be provided to the releasable retainer by coupling to an "indirect vacuum inlet" which communicates with the aspiration channel of the releasable retainer through an "aspiration circuit."

According to the invention, an "aspiration circuit" communicates with and provides a vacuum to the aspiration channel of the releasable retainer from the aspiration source. In general, coupling the aspiration source to a direct vacuum inlet at each releasable retainer provides a vacuum to the individual releasable retainers in a "parallel" arrangement. In contrast, coupling an aspiration source to an indirect vacuum inlet and through an aspiration circuit provides a vacuum to the releasable retainers in a "series" arrangement.

The aspiration circuit can be external or internal to the frame. In one embodiment, an "internal aspiration circuit" is a hollow channel coursing through the elbow region and arms of the frame. According to this embodiment, one or more indirect vacuum inlets are preferably situated at or near the elbow region and communicate with the hollow channel in the frame. The wall of the channel (frame) can include ports which are in fluid flow communication with the outside of the frame. The ports can be positioned to communicate directly with the aspiration channels of the releasable retainers. Alternatively, the aspiration circuit can be continued through the pod which would include one or more ports that communicate with the aspiration channel of the releasable retainer. If fewer releasable retainers are used than the number of ports in the wall of the frame or pod, the unused ports can be sealed using a "plug" made of plastic, rubber or other suitable material.

In an alternative embodiment, an aspiration circuit can be external to the frame. In this embodiment, the external aspiration circuit can include one or more indirect vacuum inlets that communicate with a "manifold" that provides a vacuum to the releasable retainers directly or through the pod. As used herein "a manifold" is a hollow conduit external to the frame that can provide a vacuum to one or more releasable retainers simultaneously.

D. Arm Extenders

The length of the arms of the unibody device can be extended through use of "arm extenders" which mount to the branch or to other arm extenders. Arm extenders include, for example, frame inserts, frame telescopes, and the pod of the suction arrangement. An arm extender can be linear or non-linear.

As used herein, a "frame insert" is an extender which mounts to the branch or another extender and provides for mounting of the suction arrangement. The "insert" can be mounted using known methods including threads, latches, clasps, rings, clamps, friction fit, etc. The inserts can be solid or hollow. If the insert is used on a hollow frame having an internal aspiration circuit, the extension can be hollow to provide continuity of the aspiration circuit. Preferably, the wall of a hollow insert includes ports which are in fluid flow communication with the outside of the insert as described above for the frame. Two or more inserts can be mounted together to provide incremental increases in the length of the arm.

An arm extender can also be a "frame telescope" As used herein, a "frame telescope" is an arm extender which can slide into or around the branch or another arm extender and can slide distally from the branch to increase the length of the arm. The telescope can be solid or hollow. If the frame includes an internal aspiration circuit, preferably the frame telescope is hollow to maintain continuity of the aspiration circuit. A hollow frame telescope can include ports which communicate with the outside of the frame telescope as described above.

The pod of a suction arrangement can also be an arm extender. According to this embodiment, the pod can mount to the branch or to another arm extender. Hence, in addition to other functions, in some embodiments, the pod can serve to lengthen the arm. If the frame includes an internal aspiration circuit, the pod can include a hollow channel to provide continuity of the circuit to the aspiration channel of the releasable retainers. In one embodiment, two or more pods can be linked to provide incremental increases in the length of the arm. Each pod can include one or more releasable retainers.

E. Fixing Arrangement

A unibody device disclosed herein can also include a "fixing arrangement" to fix the unibody device in a desired position. The fixing arrangement can provide for manual or rigid fixation of the device.

In one embodiment, the fixing arrangement includes a "handle" that can be permanently or removably mounted to the frame at, for example, the elbow region or arm of the frame. The handle can be mounted to the frame directly or indirectly through a handle mounting bracket that directly mounts to the frame. Threads, latches, rings, clasps, clamps, friction fit or other suitable arrangement can be used to removably mount the handle to the frame. In one embodiment, the handle removably mounts to a "handle pin" that is mounted to the frame directly or indirectly as part of a handle mounting bracket.

The components of the fixing arrangement can be made out of the same material as the device or some other material suitable for the particular use of the device.

The fixing arrangement can provide for maintaining the unibody device in a fixed position by hand holding the handle. Alternatively, fixing arrangement can include components to rigidly fix the device in position. During a surgical procedure, the unibody device can be rigidly fixed to retractors, brackets, surgery tables or other similar object. During cardiac surgery, a unibody device can be stabilized by fixing to a body wall retractor such as a sternal or intercostal retractor. Fixing the unibody device to a retractor can advantageously provide greater maneuverability for the surgeon.

In one embodiment, the unibody device is rigidly mounted to a body wall retractor using a fixing member. The "fixing member" can include a shapeable rod having a first and second end. By "shapeable" it is meant that the rod is malleable or rotatably articulated at one or more locations to provide a range of positions in which the unibody device can be fixed once engaged to the heart. The first end can couple to the handle or handle pin using a compression clamp and the second end can couple to the internal retractor through a compression clamp that is mounted to a retractor clamp that is attached to the internal retractor.

Illustrations of some embodiments of a unibody device according to the invention are shown in FIGS. 1 to 9. The invention will be further described with reference to the FIGs. Reference to the illustrated embodiments is not intended to limit the scope of the invention.

DETAILED DESCRIPTION OF THE ILLUSTRATED EMBODIMENTS

FIGS. 1, 4, 6 and 7 are top views of four embodiments of a unibody device according to the invention. FIG. 2 is a side view of the embodiment shown in FIG. 1; FIG. 3 is a cross-sectional view of a releasable retainer which can be used on the embodiment in FIG. 1. FIG. 5 is a side view of the embodiment shown in FIG. 4.

Figure 4:
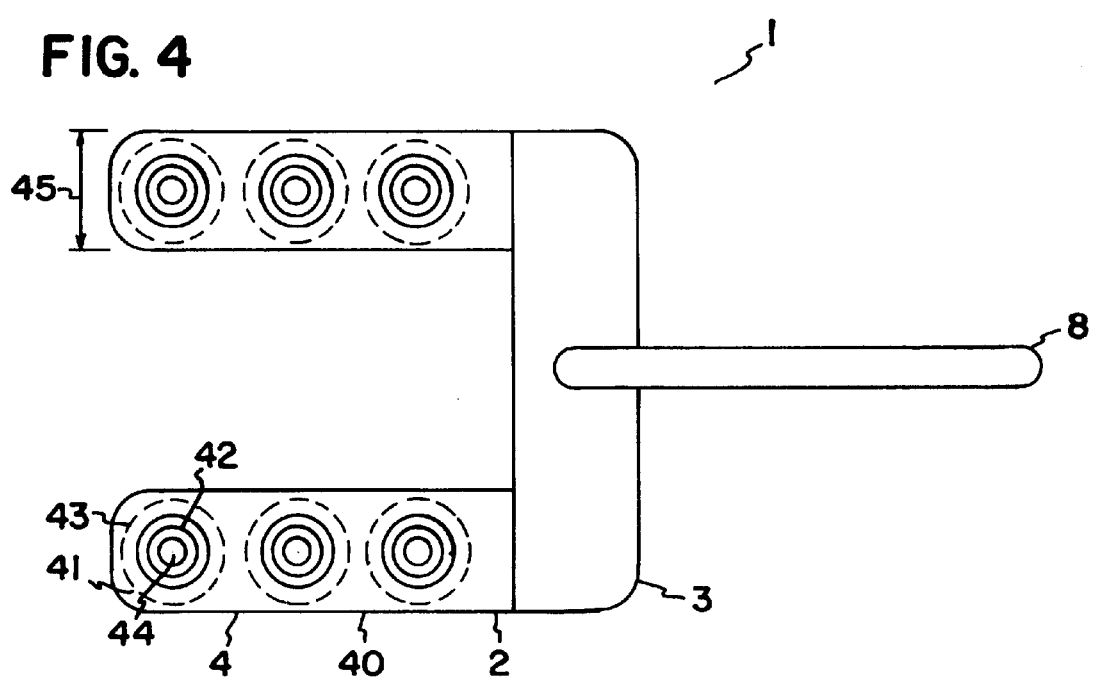
FIG. 4 is a top plan view of a second embodiment of a unibody device according to the invention.
Figure 5:
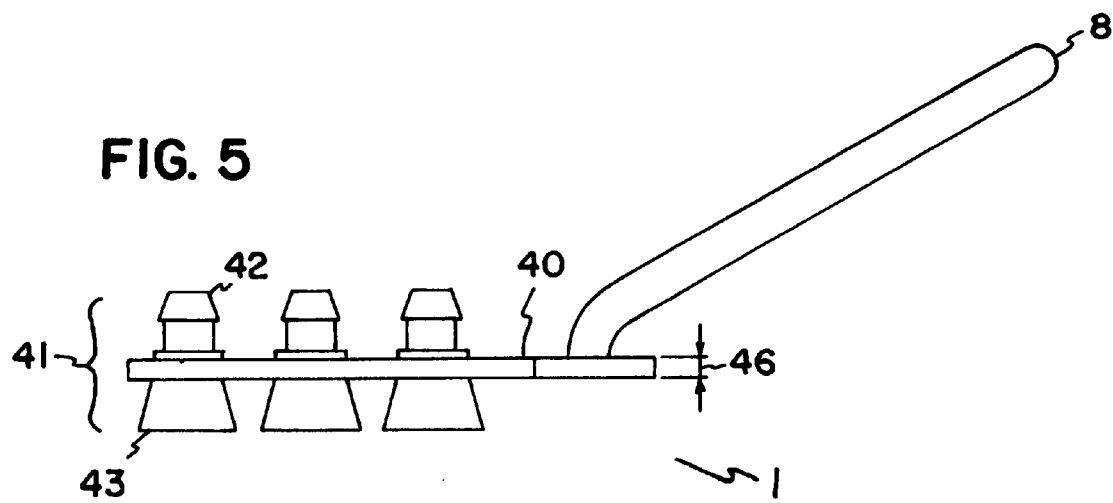
FIG. 5 is a side plan view of the embodiment of the unibody device shown in FIG. 4.

As seen in FIGS. 1, 4, 6 and 7 a unibody device 1 includes a frame 2 having an elbow region 3 and arms 4. The embodiment shown in FIGS. 1, 6 and 7 include an indirect vacuum inlet 5 at the elbow region 3 of the frame 2. The embodiment of FIGS. 1, 2 and 7 include a handle pin 6 mounted indirectly to the frame 2 through a handle mounting bracket 7 for mounting a removable handle (the removable handle is not shown). In FIG. 6, the handle pin 5 is mounted directly to the frame 2. FIGS. 4 and 5 show a handle 8 permanently mounted to the frame 2. This handle could also be removably mounted using threads or other suitable removable mounting arrangement.

Figure 2:
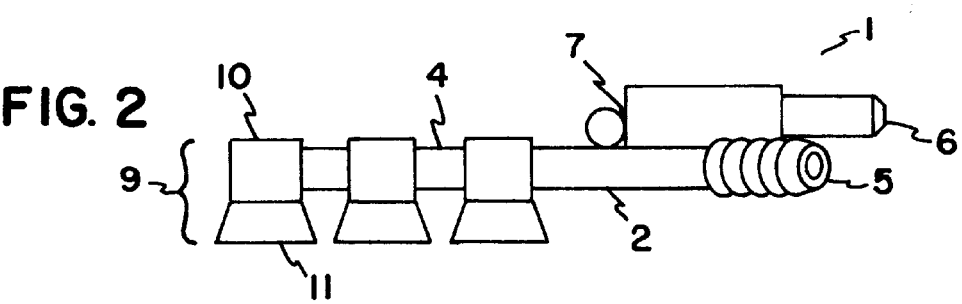
FIG. 2 is a side plan view of the embodiment of the unibody device shown in FIG. 1.
Figure 3:
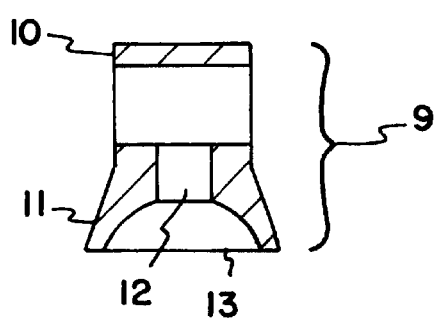
FIG. 3 is a cross-sectional view of a suction arrangement used with the unibody device shown in FIGS. 1 and 2.

Referring to the embodiment of FIGS. 1–3, the suction arrangement 9 includes a pod 10 which slides onto the frame 2 and a releasable retainer 11 for engaging a compliant material. In one embodiment, the pods can be rotated around the longitudinal axis of the arms to conform to the surface contours of the compliant body. FIG. 3 is a cross-sectional view of a suction arrangement 9 which has a pod 10 with a releasable retainer 11. In this embodiment, the releasable retainer 11 is a suction cup and it includes an aspiration channel 12 through the center of the suction cup to provide a vacuum at the contact surface 13 of the suction cup. This embodiment of the frame 2 is prepared from hollow tubing and includes an internal aspiration circuit (not shown). The embodiments of FIGS. 6 and 7 also include internal aspiration circuits (not shown). The ports in the wall of the frame which provide fluid flow communication from the internal aspiration circuit to the outside of the wall are not shown in FIGS. 1, 2, 6 and 7.

In the embodiment of FIGS. 1–2, the length of the unibody device is about 90 mm from the apex to the distal end of the arms. The arms are about 23 mm apart at the widest point. This embodiment was prepared from stainless steel tubing that has an outside diameter of 6 mm and an inside diameter of about 4 mm.

FIG. 5 is a side view of the embodiment of FIG. 4 showing a unibody device 1, which has a solid frame 40 lacking an internal aspiration circuit. The suction arrangement 41 of FIGS. 4 and 5 include a pod 42 that is integrated with the releasable retainer 43. The composition of the integrated suction arrangement 41 shown can be prepared from, for example, silicone rubber. Rather than having an internal aspiration circuit as in the embodiments of FIGS. 1, 6 and 7, vacuum can be applied to the aspiration channel 44 through the pod 42 using a manifold having an indirect vacuum inlet to provide a vacuum to multiple releasable retainers ("series") (not shown). Alternatively, in an embodiment not shown, the vacuum can be applied to the releasable retainers 43 by coupling the aspiration source directly to each suction arrangement 41 individually ("parallel").

In the embodiment of FIGS. 4 and 5, the width 45 of the frame material is about 12 mm and the thickness 46 is about 3 mm.

The embodiment of a unibody device shown in FIG. 6 includes suction arrangements 50 having pods 51 that are integrated with the frame 2 by, for example, brazing. The releasable retainer 52 is preferably removable from the pod 51. If it is desired to use fewer releasable retainers than the number of pods, a "plug" of plastic, rubber or other suitable sealing material can be used to seal the port (not shown) on the unused pods. Also note that in contrast to the embodiment of FIGS. 1, 4 and 7, the releasable retainers 52 of FIG. 6 are mounted outside the perimeter of the frame 2 rather than directly beneath the frame.

FIG. 7 is a top plan view of a unibody device having arm extenders 60 and 61 in the form of pods 62, which link together to extend the length of the arm 4. FIG. 8 is a cross-sectional view representative of the first and second arm extenders 60 and 61. As shown in FIG. 8, the pod 62 of this embodiment, includes a continuation 63 of the internal aspiration circuit (not shown) from the indirect vacuum inlet 5. The continuation 63 of the internal aspiration circuit of the pod 62 is in fluid flow communication with the aspiration channel 64 of the releasable retainer 65. In the embodiment of FIG. 8, the wall 66 of the distal end 67 of the pod 62 is narrowed relative to the proximal end 68 of the continuation 63 of the aspiration circuit to permit coupling of the arm extenders 60 and 61 to extend the arms 4. This same arrangement can be used to mount the arm extenders to the branch 69. In this embodiment, a terminal pod extender (not shown) can be used that has a continuation 63 of the aspiration circuit that is sealed at the distal end 67 of the pod 62 to maintain a vacuum.

Figure 9:
FIG. 9 is an illustration of a unibody device positioned to immobilize a region of the anterior epicardial surface of a heart around the left anterior descending coronary artery.

FIG. 9 is a perspective view of a unibody device 1 according to FIGS. 1 and 2 engaged to a heart 23 for use during, for example, cardiac bypass graft surgery.

Figure 10:
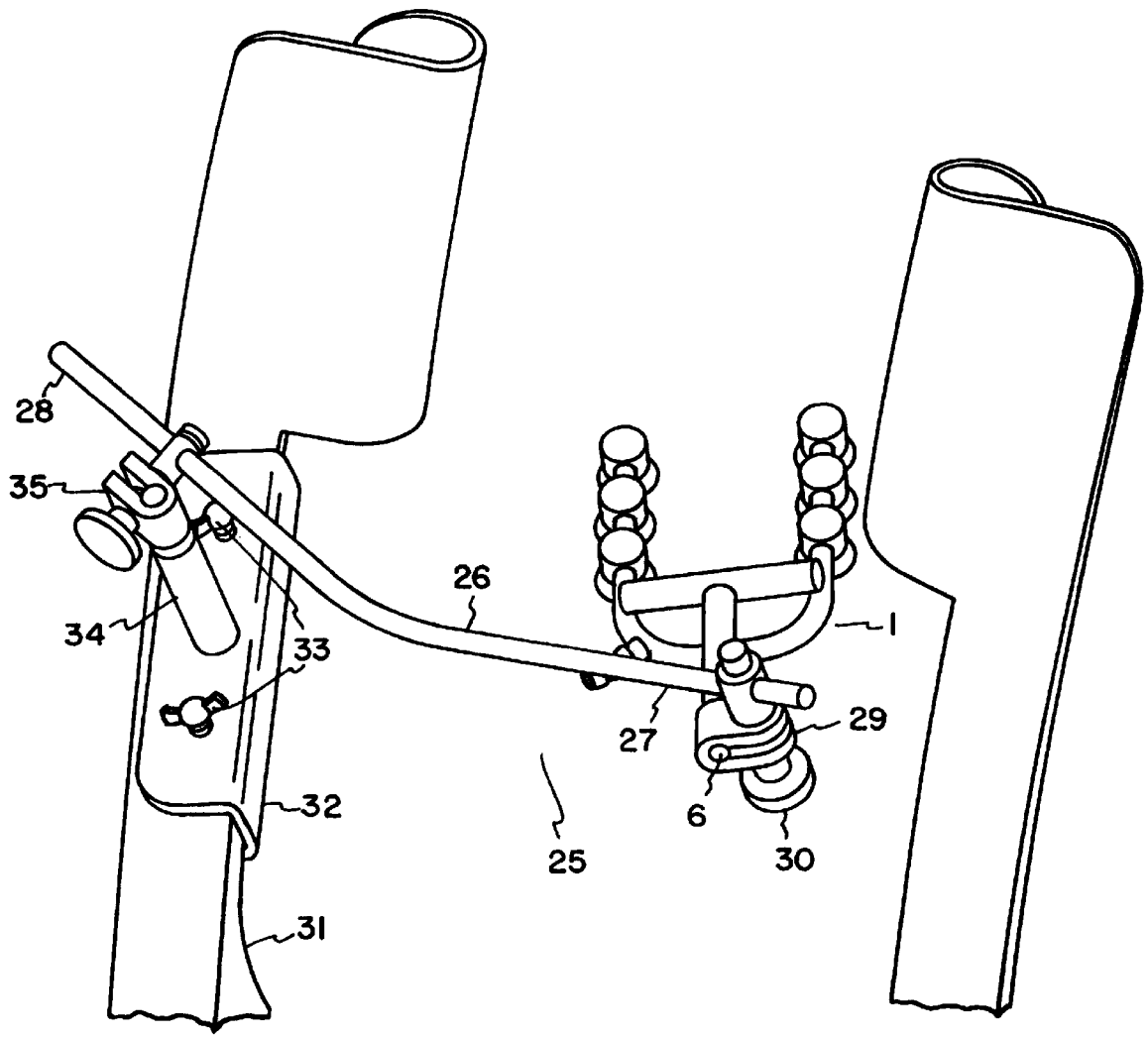
FIG. 10 is an illustration of an embodiment of a unibody device including a fixing arrangement.

FIG. 10 is an illustration of a unibody device 1 mounted to a fixing arrangement 25. According to this embodiment, a malleable fixing member 26 includes a first end 27 and a second end 28. The first end 27 is mounted to the handle pin 6 of the unibody device 1 using a first compression clamp 29 mounted to a swivel joint connector 30. The second end 28 of the fixing member 26 is mounted to a sternal retractor 31 through a retractor clamp 32. The retractor clamp 32 can be removably mounted to the retractor using, for example, wing nuts 33. The retractor clamp 32 can include a connecting post 34 on which is mounted a second compression clamp 35 to which the second end 28 of the fixing member 26 is fixed.

In one embodiment, a unibody device can be used to immobilize a localized region of an anatomical organ during a surgical procedure, for example, a cardiovascular surgery procedure. Examples of cardiovascular surgery procedures which can be performed using a unibody device of the invention are cardiac valve replacement or repair. In the case of a tricuspid valve repair or replacement, the right atrium is opened and the device is positioned and engaged to the endocardial surface of the atrium to expose the tricuspid valve. In the case of mitral valve replacement or repair, the left atrium is opened and the device is positioned and engaged to the endocardial surface to expose the mitral valve.

Another example of a cardiovascular procedure in which a unibody device of the invention can be used is coronary artery bypass graft surgery (CABG). The unibody device of the invention can also be used in limited access or minimally invasive direct coronary artery bypass (MIDCAB) procedures.

The following procedure for immobilizing a region of the heart using the unibody device of the invention is applicable whether performing CABG surgery using traditional sternotomy exposures with or without cardiopulmonary bypass, thoracotomy as well as various exposures used in MIDCAB procedures through intercostal, transcostal or epigastric (subcostal) incisions or combinations thereof.

The heart is visualized and the parietal pericardium is incised to allow exposure to the visceral pericardium or epicardium of the heart. The coronary artery to be bypassed is located and the arms of the unibody device are positioned over a region of the epicardium to longitudinally flank the artery. The releasable retainers (suction cups) are placed in contact with the epicardium and a vacuum pressure from an aspiration source is applied to engage the epicardial surface snugly against the suction cups. The amount of suction applied can be regulated at the aspiration source or by a vacuum control arrangement located between the source and the unibody device, preferably within reach of the surgeon.

During surgery the unibody device can be manually fixed or rigidly fixed through a suitable fixing arrangement. Upon completion of the bypass, the aspiration is turned off and the unibody device removed.

Typical arteries bypassed during CABG are the anterior descending coronary artery or its branches, the right coronary artery or its branches and the circumflex coronary artery or its branches. Generally, the posterior descending coronary artery and obtuse marginal branches of the circumflex coronary artery are located on the inferior/posterior aspect of the heart. Hence, to provide suitable visualization, the heart is generally rotated to expose the inferior/posterior surface.

The unibody device of the invention is suitable for retracting the heart in a rotated position. To expose the obtuse marginal branches of the circumflex coronary artery, the heart is displaced anteriorly and toward the right side of the patient. To expose the distal right coronary artery and the posterior descending branch, the inferior aspect of the heart is rotated anteriorly and superiorly. Once in the rotated position the unibody device is positioned on the epicardial surface flanking the artery to be bypassed. The releasable retainers are placed in contact with the epicardium and a vacuum pressure from an aspiration source is applied to engage the epicardial surface snugly against the suction cups. The device can be hand-held in position or, alternatively, the device can be fixed using a fixing arrangement or other suitable system. Upon completion of the procedure, the aspiration is turned off and the device removed. Known methods are used for closure.

Unlike prior art stabilization methods, the present invention does not rely on compression to immobilize the surgical field. Not only does this facilitate maintaining effective cardiac filling and output during surgery, but it can also reduce the chance of compromising myocardial perfusion which can occur due to compression of the myocardium.

Moreover, because the unibody device provides suitable immobilization of the surgical field without slowing or stopping of the heart, the need for heart lung machines or other form of circulation support is reduced. Reducing the need for CPB equipment can have significant cost saving benefits. In addition, avoiding the pathological consequences of CPB will enhance patient rehabilitation and reduce hospitalization stay costs.

All patents in the specification are indicative of the level of ordinary skill in the art to which this invention pertains and are incorporated herein by reference.

It will be apparent to one of ordinary skill in the art that many changes and modifications can be made in the invention without departing from the spirit or scope of the appended claims.

What we claim is:

1. A unibody device for immobilizing a localized region of a compliant body comprising:
   (a) a rigid frame configured to surround said localized region within a perimeter of said frame, said frame including:
      (i) an elbow region having an angle;
      (ii) a first arm extending from said elbow region;
      (iii) a second arm extending from said elbow region;
   (b) at least two suction arrangements coupled along a longitudinal axis of each of said arms, each suction arrangement including:
      (i) a pod for coupling said suction arrangement to said frame;
      (ii) a releasable retainer mounted to said pod for releasably engaging said unibody device to said compliant body; and
      (iii) an aspirator channel passing through said releasable retainer that can communicate with an aspiration source.

2. A unibody device according to claim 1 wherein one of said arms includes a branch and an arm extender.

3. A unibody device according to claim 2 wherein said arm extender is a pod.

4. The unibody device according to claim 3 further comprising a terminal pod extender.

5. The unibody device according to claim 3 wherein said pod arm extender is non-linear.

6. A unibody device according to claim 1 wherein at least one of said arms is non-linear.

7. The unibody device according to claim 1 wherein said releasable retainers are mounted outside said perimeter of said frame.

8. The unibody device according to claim 1 wherein said pods can be rotated around said longitudinal axis of the arms.

9. A unibody device according to claim 1 wherein said compliant body is an anatomical organ.

10. A unibody device according to claim 9 wherein said anatomic organ is a heart.

* * * * *